(12) United States Patent
Sun et al.

(10) Patent No.: US 12,042,324 B2
(45) Date of Patent: Jul. 23, 2024

(54) SYSTEMS AND METHODS FOR DETERMINING COUCH POSITION

(71) Applicant: SHANGHAI UNITED IMAGING HEALTHCARE CO., LTD., Shanghai (CN)

(72) Inventors: Youjun Sun, Shanghai (CN); Shitao Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 208 days.

(21) Appl. No.: 16/819,128

(22) Filed: Mar. 15, 2020

(65) Prior Publication Data

US 2020/0315565 A1 Oct. 8, 2020

(30) Foreign Application Priority Data

Mar. 15, 2019 (CN) .......................... 201910200007.0

(51) Int. Cl.
| | | |
|---|---|---|
| G16H 30/40 | (2018.01) |
| A61B 6/00 | (2024.01) |
| A61B 6/03 | (2006.01) |
| A61B 6/04 | (2006.01) |

(52) U.S. Cl.
CPC .............. *A61B 6/547* (2013.01); *A61B 6/037* (2013.01); *A61B 6/0407* (2013.01); *A61B 6/5276* (2013.01); *G16H 30/40* (2018.01)

(58) Field of Classification Search
CPC ....... A61B 6/547; A61B 6/037; A61B 6/0407; A61B 6/5276
See application file for complete search history.

(56) References Cited

U.S. PATENT DOCUMENTS

| | | | |
|---|---|---|---|
| 2016/0247274 A1* | 8/2016 | Thiruvenkadam | .... G06T 7/0012 |
| 2018/0322626 A1* | 11/2018 | Panin | ...................... G01T 1/202 |
| 2019/0059831 A1* | 2/2019 | Hu | ........................ A61B 6/0487 |
| 2019/0255362 A1* | 8/2019 | Voronenko | ........... A61N 5/1079 |

FOREIGN PATENT DOCUMENTS

| | | |
|---|---|---|
| CN | 108378852 A | 8/2018 |
| JP | H09153097 A | 6/1997 |

* cited by examiner

*Primary Examiner* — Patrick Fernandes
*Assistant Examiner* — Aminah Asghar
(74) *Attorney, Agent, or Firm* — METIS IP LLC

(57) ABSTRACT

The present disclosure may provide a method. The method may include obtaining a PET dataset relating to a subject acquired, based on a tracer species in the subject, by a PET device. The PET dataset relating to the subject may be acquired for a time period when the subject moves by moving a couch on which the subject is supported. The time period may include a first time segment and a second time segment. The method may also include determining an activity distribution set of the tracer species in the subject within the time period. The activity distribution set may include a plurality of segment activity distributions. Further, the method may include determining an offset of the couch within the second time segment with respect to the first time segment based on the activity distribution set of the tracer species.

20 Claims, 8 Drawing Sheets

```
                                          500
┌─────────────────────────────────────────────────────┐
│ Obtaining a positron emission tomography (PET) dataset relating to │
│ a subject acquired, based on a tracer species in the subject, by a │ 510
│ positron emission tomography (PET) device, wherein the PET        │
│ dataset relating to the subject is acquired for a time period when the │
│ subject moves by moving a couch on which the subject is supported │
│ with respect to the PET device, the time period comprising a first │
│ time segment and a second time segment                            │
└─────────────────────────────────────────────────────┘
                            │
                            ▼
┌─────────────────────────────────────────────────────┐
│ Determining an activity distribution set of the tracer species in the │ 520
│ subject within the time period, the activity distribution set including a │
│ plurality of segment activity distributions                       │
└─────────────────────────────────────────────────────┘
                            │
                            ▼
┌─────────────────────────────────────────────────────┐
│ Determining an offset of the couch within the second time segment │ 530
│ with respect to the first time segment based on the activity      │
│ distribution set of the tracer species                            │
└─────────────────────────────────────────────────────┘
```

FIG. 5

BACKGROUND

SYSTEMS AND METHODS FOR DETERMINING COUCH POSITION

CROSS-REFERENCE TO THE RELATED APPLICATIONS

This application claims priority of Chinese Application No. 201910200007.0, filed on Mar. 15, 2019, the contents of each of which are hereby incorporated by reference.

TECHNICAL FIELD

The present disclosure generally relates to positron emission tomography (PET) imaging, and more specifically relates to systems and methods for determining position information (e.g., a couch code) of a moving couch during the PET imaging.

BACKGROUND

A PET system may acquire PET data relating to a subject by scanning the subject. In some scenarios, the subject may be moved during a scanning by moving a couch on which the subject is supported. Position information of the moving couch may be used together with the PET data to implement functions including, e.g., filtering out incorrect lines of response (LORs) and/or coincidence events, determining one or more parameters associated with efficiency normalization of a PET device in the PET system, reconstructing a PET image, etc. Thus, it is desirable to provided systems and methods for efficiently determining position information (e.g., a couch code) of a moving couch directly using PET data.

SUMMARY

According to one aspect of the present disclosure, a system may be provided. The system may include at least one storage device including a set of instructions and at least one processor in communication with the at least one storage device. When executing the set of instructions, the at least one processor may be configured to cause the system to perform operations including: obtaining a positron emission tomography (PET) dataset relating to a subject acquired, based on a tracer species in the subject, by a positron emission tomography (PET) device, the PET dataset relating to the subject being acquired for a time period when the subject moves by moving a couch on which the subject being supported, the time period including a first time segment and a second time segment; determining an activity distribution set of the tracer species in the subject within the time period, the activity distribution set including a plurality of segment activity distributions; and determining an offset of the couch within the second time segment with respect to the first time segment based on the activity distribution set of the tracer species.

According to another aspect of the present disclosure, a method may be provided. The method may be implemented on a computing device having at least one processor, and at least one storage device. The method may include: obtaining a positron emission tomography (PET) dataset relating to a subject acquired, based on a tracer species in the subject, by a positron emission tomography (PET) device, the PET dataset relating to the subject being acquired for a time period when the subject moves by moving a couch on which the subject being supported, the time period including a first time segment and a second time segment; determining an activity distribution set of the tracer species in the subject within the time period, the activity distribution set including a plurality of segment activity distributions; and determining an offset of the couch within the second time segment with respect to the first time segment based on the activity distribution set of the tracer species.

According to another aspect of the present disclosure, a non-transitory computer readable medium may be provided. The non-transitory computer readable medium may include instructions being executed by at least one processor, causing the at least one processor to implement a method. The method may include: obtaining a positron emission tomography (PET) dataset relating to a subject acquired, based on a tracer species in the subject, by a positron emission tomography (PET) device, the PET dataset relating to the subject being acquired for a time period when the subject moves by moving a couch on which the subject being supported, the time period including a first time segment and a second time segment; determining an activity distribution set of the tracer species in the subject within the time period, the activity distribution set including a plurality of segment activity distributions; and determining an offset of the couch within the second time segment with respect to the first time segment based on the activity distribution set of the tracer species.

In some embodiments, the time period may include a plurality of time segments. The determining an activity distribution set of the tracer species in the subject within the time period may include: for each of at least two of the plurality of time segments, determining a segment activity distribution of the tracer species in the subject within the time segment, the at least two of the plurality of time segments including the first time segment and the second time segment.

In some embodiments, the determining an activity distribution set of the tracer species in the subject within the time period may further include: determining, from the PET dataset, a plurality of PET data subsets each of which corresponds to one of the plurality of time segments. For each of the at least two of the plurality of time segments, the determining a segment activity distribution of the tracer species in the subject within the time segment may include: determining the segment activity distribution of the tracer species in the subject within the time segment based on one of the plurality of PET data subsets corresponding to the time segment.

In some embodiments, the determining the offset of the couch within the second time segment with respect to the first time segment based on the activity distribution set of the tracer species may include: determining a distribution curve set based on the activity distribution set of the tracer species; and determining the offset of the couch within the second time segment with respect to the first time segment based on the distribution curve set.

In some embodiments, the distribution curve set may include a first section distribution curve corresponding to the first time segment and a second section distribution curve corresponding to the second time segment. The determining the offset of the couch within the second time segment with respect to the first time segment based on the distribution curve set may include: determining the offset of the couch within the second time segment with respect to the first time segment based on the first section distribution curve and the second section distribution curve.

In some embodiments, the determining the offset of the couch within the second time segment with respect to the first time segment based on the distribution curve set may include: determining the offset of the couch within the second time segment with respect to the first time segment by registering the second section distribution curve with the first section distribution curve using a registration algorithm.

In some embodiments, the registration algorithm may include at least one of a least squares technique or a correlation coefficient technique.

In some embodiments, each of the plurality of segment activity distributions may include a segment activity distribution of the tracer species in the subject along a direction in which the couch moves.

In some embodiments, the offset of the couch may include an offset of the couch along a direction in which the couch moves.

In some embodiments, the at least one processor may be further configured to cause the system to perform the operations including: obtaining first position information of the couch within the first time segment; and determining second position information of the couch within the second time segment based on the first position information and the offset.

In some embodiments, the determining an activity distribution set of the tracer species in the subject within the time period may include: determining a plurality of time segments based on at least one of a velocity of the couch or an accuracy of the second position information, the plurality of time segments including the first time segment and the second time segment.

In some embodiments, the determining an activity distribution set of the tracer species in the subject within the time period may include: identifying, based on the PET dataset, a plurality of coincidence events along a direction in which the couch moves; and determining the activity distribution set of the tracer species in the subject based on the plurality of coincidence events.

In some embodiments, the determining an activity distribution set of the tracer species in the subject based on the plurality of coincidence events may include: identifying, among the plurality of coincidence events, coincidence events occurred in one or more cross-sections of the subject perpendicular to the direction in which the couch moves; and determining the activity distribution set of the tracer species in the subject based on the identified coincidence events.

In some embodiments, the determining an activity distribution set of the tracer species in the subject based on the plurality of coincidence events may include: determining a time-of-flight (TOF) dataset of the plurality of coincidence events; determining location information of the plurality of coincidence events based on the time-of-flight (TOF) dataset; and determining the activity distribution set of the tracer species in the subject based on the location information of the plurality of coincidence events.

In some embodiments, the at least one processor may be configured to cause the system to perform additional operations including: normalizing the plurality of coincidence events; and determining the activity distribution set of the tracer species in the subject based on the normalized coincidence events.

In some embodiments, the PET device may include a plurality of detectors. The normalizing the plurality of coincidence events may include: determining an efficiency distribution of the plurality of detectors based on a uniform phantom; and normalizing the plurality of coincidence events based on the efficiency distribution.

In some embodiments, the determining an activity distribution set of the tracer species in the subject within the time period may include: identifying a part of the PET dataset corresponding to a region of the subject; and determining the activity distribution set of the tracer species in the subject based on the identified part of the PET dataset.

In some embodiments, the region of the subject may include at least one of the head or the bladder of the subject.

According to another aspect of the present disclosure, a system may be provided. The system may include at least one storage device including a set of instructions and at least one processor in communication with the at least one storage device. When executing the set of instructions, the at least one processor may be configured to cause the system to perform operations including: obtaining a positron emission tomography (PET) dataset relating to a subject acquired when a couch supporting the subject moves within a time period; acquiring an activity distribution curve set based on the PET dataset, the activity distribution curve set including a plurality of section activity distribution curves; and determining a position offset of the couch based on the activity distribution curve set.

According to another aspect of the present disclosure, a method may be provided. The method may be implemented on a computing device having at least one processor, and at least one storage device. The method may include: obtaining a positron emission tomography (PET) dataset relating to a subject acquired when a couch supporting the subject moves within a time period; acquiring an activity distribution curve set based on the PET dataset, the activity distribution curve set including a plurality of section activity distribution curves; and determining a position offset of the couch based on the activity distribution curve set.

According to another aspect of the present disclosure, a non-transitory computer readable medium may be provided. The non-transitory computer readable medium may include instructions being executed by at least one processor, causing the at least one processor to implement a method. The method may include: obtaining a positron emission tomography (PET) dataset relating to a subject acquired when a couch supporting the subject moves within a time period; acquiring an activity distribution curve set based on the PET dataset, the activity distribution curve set including a plurality of section activity distribution curves; and determining a position offset of the couch based on the activity distribution curve set.

In some embodiments, the system may be further directed to perform the operations including: determining a couch code of the couch based on the position offset and a reference couch code.

In some embodiments, the time period may include a plurality of time segments. The acquiring the activity distribution curve set based on the PET dataset within the time period may include: for each of at least two of the plurality of time segments, determining a section activity distribution curve.

In some embodiments, the at least two of the plurality of time segments may include a first time segment and a second time segment. The position offset of the couch may include a position offset of the couch within the second time segment with respect to the first time segment. The reference couch code may include a couch code of the couch within the first time segment.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for determining an offset of a couch according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
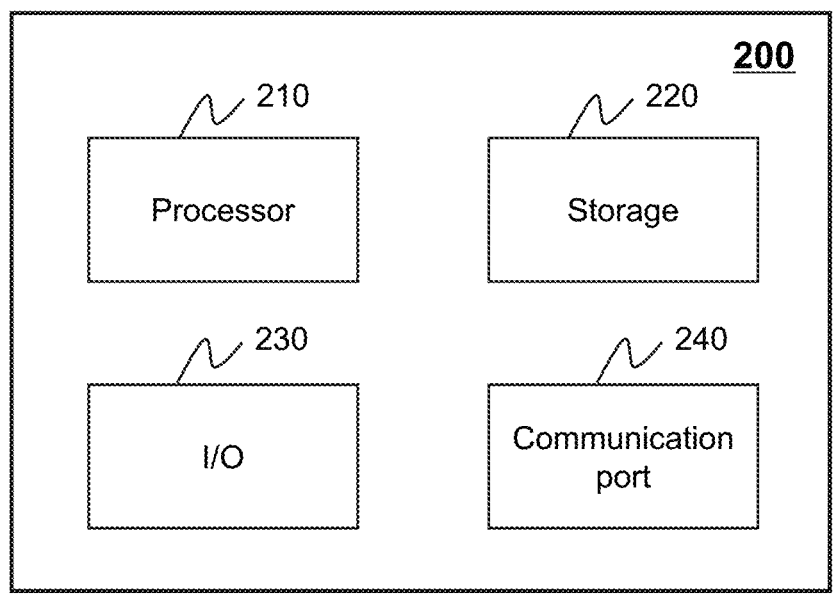
FIG. 2 is a schematic diagram illustrating exemplary hardware and/or software components of a computing device on which the processing device may be implemented according to some embodiments of the present disclosure.

Generally, the term "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a positron emission tomography (PET) system, a single positron emission tomography (SPET) system, etc. The multi-modality imaging system may include, for example, a positron emission tomography-magnetic resonance imaging (PET-MRI) system, a single photon emission computed tomography-magnetic resonance imaging (SPECT-MRI) system, etc. In some embodiments, the medical system may include a treatment system. The treatment system may include a treatment plan system (TPS), image-guided radiotherapy (IGRT), etc. The image-guided radiotherapy (IGRT) may include a treatment device and an imaging device. The treatment device may include a linear accelerator, a cyclotron, a synchrotron, etc., configured to perform radiotherapy on a subject. The treatment device may include an accelerator of species of particles including, for example, photons, electrons, protons, or heavy ions. The imaging device may include a PET device, a SPET device, etc.

Figure 1:
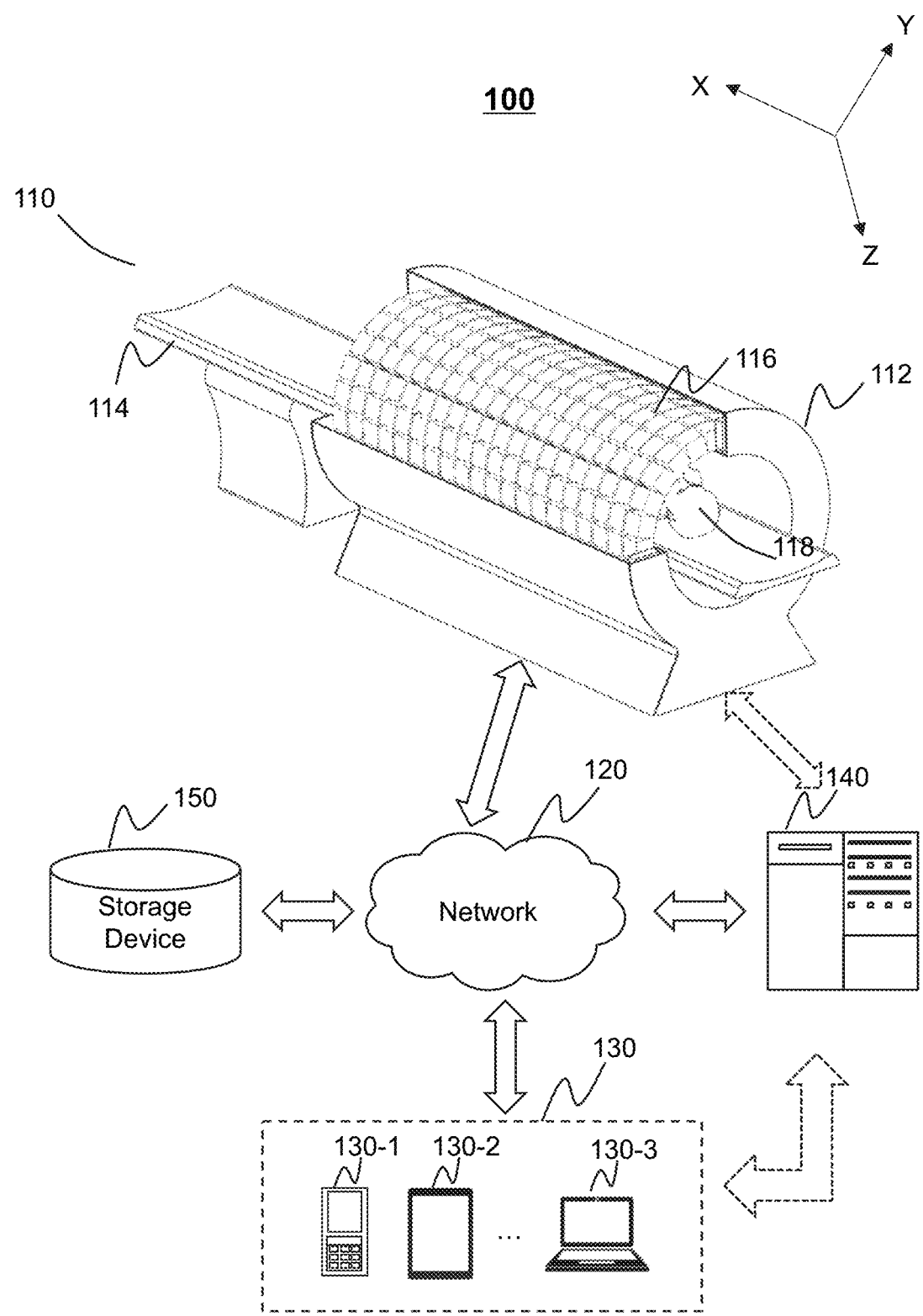
FIG. 1 is a schematic diagram illustrating an exemplary positron emission tomography (PET) system according to some embodiments of the present disclosure.

An aspect of the present disclosure relates to methods and systems for determining an offset (e.g., position offset) of a couch (also referred to as a couch offset) in a PET system. A PET dataset relating to a subject may be obtained. For example, a tracer species may be injected into the subject, and then the PET dataset may be acquired by scanning the subject using a PET device for a time period when the subject is moved within the detection region (e.g., detection region 117 as illustrated in FIG. 1) of the PET device by moving the couch on which the subject is supported. Further, an activity distribution set of the tracer species in the subject within the time period may be determined based on the PET dataset. In some embodiments, the activity distribution set may include at least a first segment activity distribution corresponding to a first time segment of the time period and a second segment activity distribution corresponding to a second time segment of the time period. Further, a couch offset within the second time segment with respect to the first time segment may be determined based on the first segment activity distribution and the second segment activity distribution. Therefore, the offset of the couch may be determined directly using the PET dataset, thereby obviating the need to employ an additional device, which in turn may reduce the amount of data to be processed to determine a couch offset during a scanning.

In some embodiments of the present disclosure, the offset of the couch may be determined using only a part of the PET dataset, e.g., a first PET data subset corresponding to the first time segment and a second PET data subset corresponding to a second time segment, thereby increasing the efficiency of the determination of an offset of the couch during a scanning compared to using the entire PET dataset.

In some embodiments of the present disclosure, the accuracy of the determination of a couch offset may be adjusted by adjusting the time length of a time segment of the time period, e.g., the first time segment and/or the second time segment. For example, if the moving speed of the couch during a time segment is relatively fast, the time length of the time segment may be adjusted to a relatively small value such that the accuracy of the determined couch offset may satisfy an accuracy requirement. In some embodiments, provided that the accuracy requirement is satisfied, the efficiency for determining a couch offset may be adjusted or improved by adjusting or increasing the time length of a time segment involved in the couch offset determination.

Another aspect of the present disclosure relates to methods and systems for determining an offset (e.g., position offset) of a couch (also referred to as a couch offset) in a PET system. A PET dataset relating to a subject may be obtained. The PET dataset may be acquired when the couch moves within a time period. An activity distribution curve set (or referred to as distribution curve set) may be acquired based on the PET dataset. The activity distribution curve set may be a representation of an activity distribution set (e.g., an activity distribution set of a tracer species in the subject). The activity distribution curve set may include a plurality of section activity distribution curves (or referred to as section distribution curve). A position offset of the couch may be determined based on the activity distribution curve set. For example, the position offset may include a position offset relating to two of the plurality of section activity distribution curves. In some embodiments, a couch code of the couch may be further determined based on the position offset and a reference couch code.

FIG. 1 is a schematic diagram illustrating an exemplary positron emission tomography (PET) system according to some embodiments of the present disclosure. As illustrated in FIG. 1, the PET system 100 may include a PET device 110, a network 120, a terminal 130, a processing device 140, and a storage device 150. The components in the PET system 100 may be connected in various ways. Merely by way of example, the PET device 110 may be connected to the processing device 140 through the network 120. As another example, the PET device 110 may be connected to the processing device 140 directly as indicated by the bi-directional arrow in dotted lines linking the PET device 110 and the processing device 140. As a further example, the storage device 150 may be connected to the processing device 140 directly or through the network 120. As still a further example, the terminal 130 (e.g., terminals 130-1, 130-2, 130-3, etc.) may be connected to the processing device 140 directly (as indicated by the bi-directional arrow in dotted lines linking the terminal 130 and the processing device 140) or through the network 120.

The PET device 110 may include a gantry 112, a couch 114, and a detector module 116. The gantry 112 may support the detector module 116. The detector module 116 may include one or more detector rings along the axial dimension of the PET device, (e.g., the X-axis direction illustrated in FIG. 1), which form a field of view (FOV) of the PET device 110. Each of the one or more detector rings may include multiple detectors arranged along the circumference of the detector ring. For example, the detector may include a scintillation detector (e.g., a cesium iodide detector), a gas detector, or the like, or any combination thereof.

A subject 118 may be placed on the couch 114 and moved into a detection region 117 surrounded by the detector module 116. In some embodiments, the field of view (FOV) (e.g., 2 meters) of the PET device 110 may be greater than or equal to the length of the entire subject. In some embodiments, the FOV of the PET device 110 may be smaller than the length of the entire subject.

In some embodiments, the subject 118 may be moved by moving the couch 114 within the detection region 117 of the PET device 110. In some embodiments, the couch may move along the axial dimension of the PET device 110 (e.g., the X-axis direction illustrated in FIG. 1). For example, the couch may move along the positive X-axis direction or the negative X-axis direction. As another example, the couch may move back and forth along the X-axis direction. In some embodiments, the couch may move at a constant velocity or a varying velocity, e.g., a velocity that changes with time. For example, the moving speed of the couch may be 1.5 mm/s for scanning the head of the subject; while the moving speed of the couch may be 1.0 for continuously scanning the torso.

The subject 118 may be a biological subject (e.g., a patient, an animal) or a non-biological subject (e.g., a phantom). In some embodiments, the subject may include a specific part, organ, and/or tissue of the subject. For example, the subject may include the head, the bladder, the brain, the neck, the torso, a shoulder, an arm, the thorax, the heart, the stomach, a blood vessel, soft tissue, a knee, a foot, or the like, or any combination thereof, of a patient. In the present disclosure, "object" and "subject" are used interchangeably.

Before a PET scanning, the subject 118 may be injected with a tracer species. The tracer species may refer to a radioactive substance that decays and emits positrons. In some embodiments, the tracer species may be radioactively marked radiopharmaceutical, which is a drug having radioactivity and is administered to the subject 118. For example, the tracer species may include fluorine-18 ($^{18}$F) fluorodeoxyglucose (FDG), etc.

During the PET scanning, pairs of photon (e.g., gamma photons) may result from the annihilation of positrons originating from the tracer species in the subject 118. A pair of photons may travel in opposite directions. At least a part of the pairs of photons may be detected and/or registered by the detectors in the detector module 116. A coincidence event may be recorded when a pair of photons generated by the positron-electron annihilation are detected within a coincidence time window, e.g., within 6 to 12 nanoseconds. An LOR corresponding to the coincidence event may include a line connecting two detectors that have detected and/or registered a pair of photons. The LOR may indicate a traveling path of the pair of photons.

The network 120 may facilitate exchange of information and/or data. In some embodiments, one or more components of the PET system 100 (e.g., the PET device 110, the terminal 130, the processing device 140, or the storage device 150) may send information and/or data to another component(s) in the PET system 100 via the network 120. For example, the processing device 140 may obtain, via the network 120, a PET dataset relating to the subject 118 from the PET device 110. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, or the like, or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the PET system 100 may be connected to the network 120 to exchange data and/or information.

The terminal 130 may include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the PET device 110. In some embodiments, the terminal 130 may operate the PET device 110 via a wireless connection. In some embodiments, the terminal 130 may receive information and/or instructions inputted by a user, and send the received information and/or instructions to the PET device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the PET device 110, the terminal 130, or the storage device 150. For example, the processing device 140 may determine an activity distribution set including a plurality of segment activity distributions of the tracer species in the subject within the time period. Further, the processing device 140 may determine an offset (e.g., position offset) of the couch within a second time segment of the time period with respect to a first time segment of the time period based on the activity distribution set including the plurality of segment activity distributions of the tracer species. As another example, the processing device 140 may determine an activity distribution curve set including a plurality of section activity distribution curves. Further, the processing device 140 may determine a position offset of the couch based on the activity distribution curve set.

In some embodiments, the processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the PET device 110, the terminal 130, and/or the storage device 150 via the network 120. As another example, the processing device 140 may be directly connected to the PET device 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the PET system 100 (e.g., the terminal 130, the processing device 140). One or more components of the PET system 100 may access the data or instructions stored in the storage device 150 via the network 120. In some embodiments, the storage device 150 may be directly connected to or communicate with one or more components of the PET system 100 (e.g., the terminal 130, the processing device 140). In some embodiments, the storage device 150 may be part of the processing device 140.

FIG. 2 is a schematic diagram illustrating exemplary hardware and/or software components of a computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the PET device 110, the terminal 130, the storage device 150, and/or any other component of the PET system 100. For example, the processor 210 may determine an activity distribution set including a plurality of segment activity distributions of the tracer species in the subject within the time period. Further, the processing device 140 may determine an offset (e.g., position offset) of the couch within a second time segment of the time period with respect to a first time segment of the time period based on the activity distribution set including the plurality of segment activity distributions of the tracer species. As another example, the processing device 140 may determine an activity distribution curve set including a plurality of section activity distribution curves within the time period. Further, the processing device 140 may determine a position offset of the couch based on the activity distribution curve set.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the PET device 110, the terminal 130, the storage device 150, or any other component of the PET system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the PET device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
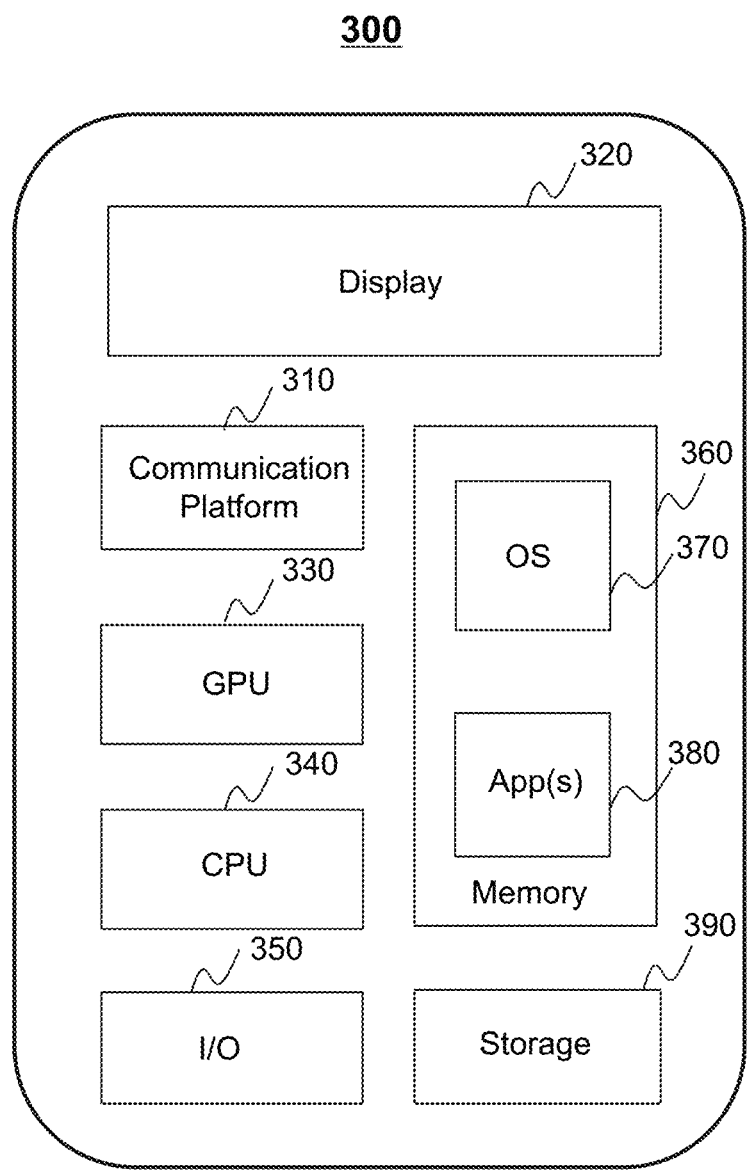
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the PET system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to determine the offset of the couch as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
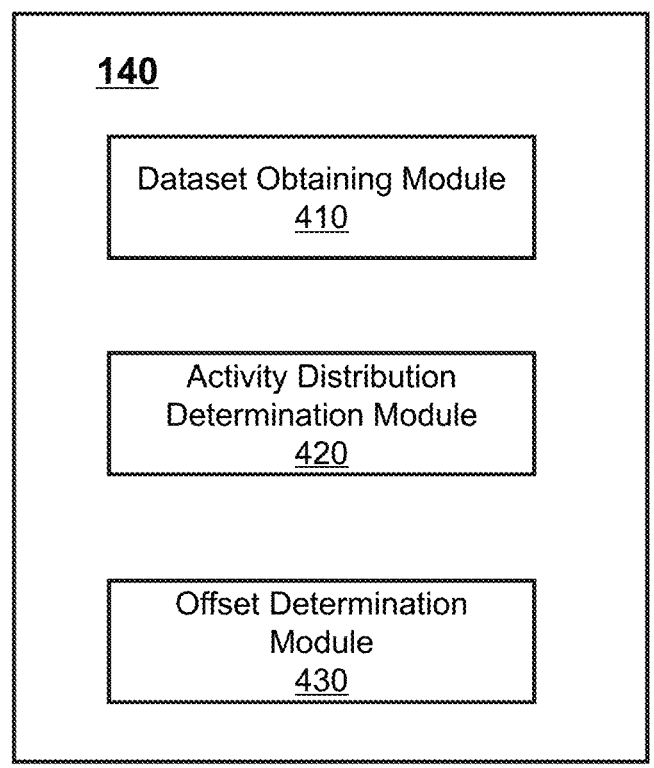
FIG. 4 is a schematic block diagram illustrating an exemplary processing device according to some embodiments of the present disclosure.

FIG. 4 is a schematic block diagram illustrating an exemplary processing device 140 according to some embodiments of the present disclosure. The processing device 140 may include a dataset obtaining module 410, an activity distribution determination module 420, and an offset determination module 430.

The dataset obtaining module 410 may be configured to obtain a positron emission tomography (PET) dataset relating to a subject (e.g., the subject 118). In some embodiments, the PET dataset may be acquired when a couch (e.g., the couch 114) supporting the subject moves within a time period. For example, the PET dataset may be acquired by scanning the subject using a PET device for the time period when the subject is moved within the detection region (e.g., detection region 117 as illustrated in FIG. 1) of the PET device by moving the couch on which the subject is supported. In some embodiments, the PET device may acquire the PET dataset by scanning at least a portion of the subject. For example, the PET device may acquire the PET dataset by scanning the entire subject. Accordingly, the PET dataset may include a PET dataset of the entire subject. As another example, the PET device may acquire the PET dataset by scanning a part of the subject. The PET dataset may include a PET dataset of the part of the subject.

For example, the PET dataset may include a plurality of LORs relating to the subject, a plurality of coincidence events relating to the subject, time information of a plurality of coincidence events relating to the subject, location information of a plurality of coincidence events relating to the subject, or the like, or any combination thereof. In some embodiments, time information may include a time-of-flight (TOF) dataset of the plurality of coincidence events. The TOF dataset of one of the plurality of coincidence events may include time points when a pair of photons corresponding to the coincidence event is detected by two of a plurality of detectors in the PET device, respectively, a difference between the time points, or the like, or any combination thereof.

In some embodiments, location information of one of the plurality of coincidence events may include locations of two of the plurality of detectors that detect a pair of photons corresponding to the coincidence event, respectively, a location where the coincidence event occurs, or the like, or any combination thereof. In some embodiments, the location of a detector may be represented by a serial number of the detector. Merely by way of example, as described in connection with FIG. 1, the PET device may include one or more detector rings, each of which may have multiple detectors. Each of the one or more detector rings may have a first serial number, and each of the multiple detectors in a ring may have a second serial number. The location of the detector may be represented by the first serial number and the second serial number.

The activity distribution determination module 420 may be configured to determine an activity distribution set of the tracer species in the subject within the time period. In some embodiments, different positions of the subject may have different uptake of the tracer species, that is, different counts of the annihilation events have occurred at different positions of the subject. The activity distribution set may correspond to a distribution set of the uptake of the tracer species at different positions of the subject, or a distribution set of the annihilation events having occurred at different positions of the subject. In some embodiments, the activity distribution set may include a plurality of segment activity distributions. Each of the plurality of segment activity distributions may correspond to one of a plurality of time segments included in the time period and one of a plurality of PET sub datasets included in the PET dataset. In some embodiments, the uptake of the tracer species at a position of the subject may be represented by a count of coincidence events having occurred in the position detected by the plurality of detectors in the PET device. Accordingly, the activity distribution determination module 420 may determine the activity distribution set (i.e., the plurality of segment activity distributions) based on the plurality of coincidence events included in the PET dataset.

In some embodiments, the activity distribution set may include an activity distribution set of the tracer species in the subject along a direction in which the couch moves. In some embodiments, the activity distribution determination module 420 may determine the activity distribution set based on coincidence events having occurred along the direction.

In some embodiments, the activity distribution determination module 420 may determine a segment activity distribution based on coincidence events having occurred in one or more cross-sections (also referred to as "direct slice") of the subject perpendicular to a direction (e.g., the X-axis direction illustrated in FIG. 1) in which the couch moves among coincidence events (also referred to as segment coincidence events) identified within a time segment corresponding to the segment activity distribution. As used herein, a coincidence event having occurred in a cross-section may indicate that a pair of photons corresponding to the coincidence event may be detected by two detectors in the same detector ring, that is, an LOR corresponding to the coincidence event may be perpendicular to the direction.

In some embodiments, the activity distribution determination module 420 may determine the segment activity distribution based on location information of the segment coincidence events. For example, location information of a segment coincidence event may include a location where the segment coincidence event occurs at an LOR corresponding to the segment coincidence event. As described above, the activity distribution set may correspond to the distribution set of the uptake of the tracer species in different positions of the subject. The uptake of the tracer species at a position of the subject may be represented by a count of coincidence events having occurred at the position detected by the plurality of detectors in the PET device. The activity distribution determination module 420 may determine the uptake of the tracer species in the one or more cross-sections (i.e., the direct slices) based on the segment coincidence events having occurred in the one or more sections and/or the location information of the segment coincidence events and further determine the segment activity distribution based on the uptake of the tracer species.

The offset determination module 430 may be configured to determine an offset (e.g., a position offset) of the couch (also referred to as "couch offset") within a second time segment (or a corresponding PET data subset) of the time period with respect to a first time segment (or a corresponding PET data subset) of the time period based on the activity distribution set including the plurality of segment activity distributions of the tracer species. In the present disclosure, "offset," "position offset," and "couch offset" are used interchangeably. In some embodiments, the offset determination module 430 may also determine a distribution curve set based on the activity distribution set including the plurality of segment activity distributions, and further determine the offset of the couch accordingly. In some embodiments, values in the X-axis of the distribution curve set may represent position information of positions along the direction, and values in the Y-axis of the distribution curve set may represent uptake of the tracer species in cross-sections of the subject perpendicular to the direction. In some embodiments, each of the values in the Y-axis of the section distribution curve may include the count of coincidence events having occurred in a corresponding cross-section of the subject perpendicular to the direction. For example, the coincidence events having occurred in the corresponding cross-section may include coincidence events having occurred in different positions of the corresponding cross-section. Each of the values in the X-axis of the distribution curve set may be expressed in terms of a value in the length dimension along the direction (e.g., centimeter, millimeter) or a dimensionless value (e.g., a normalized value).

Similar to the activity distribution set, the distribution curve set may include a plurality of section distribution curves, each of which may correspond to one of the plurality of segment activity distributions. In some embodiments, at least two PET sub datasets may correspond to coincidence events having occurred at regions of the subject that at least partially overlap. The section distribution curve may be a one-dimensional function along the X-axis. The only difference between different section distribution curves (or a portion of each of the section distribution curves) corresponding to a same region of the subject may be an offset between the section distribution curves along the X-axis. For brevity, two section distribution curves that correspond to a same region of a subject are referred to as two corresponding section distribution curves. For brevity, portions of two section distribution curves in which a portion from each of the section distribution curves corresponds to a same region of a subject are referred to as corresponding portions of the section distribution curves. For brevity, an offset between corresponding section distribution curves (or corresponding portions of the section distribution curves) is referred to as a distribution curve offset.

In some embodiments, the offset determination module 430 may determine an offset between corresponding section distribution curves (or corresponding portions of the section distribution curves) by registering the corresponding section distribution curves (or the corresponding portions of the section distribution curves) using a registration algorithm. In some embodiments, based on a distribution curve offset between two corresponding section distribution curves (or corresponding portions of the section distribution curves), the offset determination module 430 may determine a corresponding offset of the couch. For example, a distribution curve offset may be equal to a corresponding offset.

As used herein, the first time segment and the second time segment may be two of the plurality of time segments. The plurality of segment activity distributions may include at least a first segment activity distribution corresponding to the first time segment and a second segment activity distribution corresponding to the second time segment. The plurality of distribution curves may include at least a first section distribution curve corresponding to the first time segment and a second section distribution curve corresponding to the second time segment. The first section distribution curve and the second section distribution curve may include data of a same region of the subject. The processing device 140 may determine the offset of the couch based on the offset between the first segment activity curve and the second segment activity curve corresponding to the same region of the subject, and the offset of the couch accordingly. For instance, the distribution curve offset may be equal to the offset of the couch.

In some embodiments, the offset determination module 430 may also determine second position information of the couch within the second time segment based on the couch offset and first position information of the couch within the time segment. As used herein, the first position information or the second position information of the couch may include a first position (e.g., a first couch code) within the first time segment or a second position (e.g., a second couch code) within the second time segment of the couch along the direction. The first couch code (or the second couch code) may be the first position (or second position) of the couch or a dimensionless value (e.g., a normalized value) corresponding to the first position (or second position) of the couch. For example, the first position information (e.g., the first position) or the second position information (e.g., the second position) may be expressed in terms of a value in the length dimension along the direction or a dimensionless value (e.g., a normalized value). In some embodiments, the first position information of the couch may be known, and the offset determination module 430 may determine a value representing the second position based on the first position and the couch offset.

In some embodiments, before determining the activity distribution set (i.e., the plurality of segment activity distributions), the offset determination module 430 may identify a first part of the PET dataset corresponding to a region of the subject, and determine the activity distribution set accordingly. In some embodiments, the uptake of the tracer species in some part of the subject may exceed an uptake threshold, e.g., the head, the bladder, etc.

In some embodiments, before determining the activity distribution set, the offset determination module 430 may normalize the coincidence events to compensate for the effect of the non-uniform efficiencies of the plurality of detectors. In some embodiments, the processing device 140 may assess the efficiencies of the plurality of detectors using a uniform phantom. As used herein, a uniform phantom has a substantially constant uptake of the tracer species at all positions of the uniform phantom. As used herein, a substantially constant uptake of the tracer species by a phantom indicates that the variation between the uptakes of the tracer species throughout the phantom is below a threshold, e.g., below 20%, or below 10%, etc. In some embodiments, the offset determination module 430 may determine an efficiency distribution of the plurality of detectors based on PET data acquired by scanning the uniform phantom. For example, the PET device may scan the uniform phantom which may pass the entire FOV of the PET device and a PET dataset relating to the uniform phantom may be obtained. The processing device 140 may determine the efficiency distribution based on the PET dataset relating to the uniform phantom.

In some embodiments, as described above, the activity distribution set may be represented in the form of an activity distribution curve set (or referred to as distribution curve set). The activity distribution curve set may include the plurality of section activity distribution curves each of which corresponds to one of the plurality of segment activity distributions. The distribution determination module 420 may acquire the activity distribution curve set. The offset determination module 430 may determine an offset (e.g., a position offset) of the couch based on the plurality of section activity distribution curves.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of the processing device 140. As another example, each of the components of the processing device 140 may include a storage device. Additionally or alternatively, the components of the processing device 140 may share a common storage device.

FIG. 5 is a flowchart illustrating an exemplary process for determining an offset of a couch according to some embodiments of the present disclosure. In some embodiments, the process 500 may be implemented in the PET system 100 illustrated in FIG. 1. For example, the process 500 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing devices 140. The operations of the illustrated process 500 presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 140 (e.g., the dataset obtaining module 410) may obtain a positron emission tomography (PET) dataset relating to a subject (e.g., the subject 118). The PET dataset may be acquired by a positron emission tomography (PET) device (e.g., the PET device 110) based on a tracer species in the subject. As described in connection with FIG. 1, the tracer species may refer to a radioactive substance that may decay and emit positrons. In some embodiments, the PET dataset may be acquired after the tracer species is injected into the subject and further the subject is scanned by the PET device. Pairs of photons may result from the annihilation of positrons originating from the tracer species in the subject 118. A coincidence event may be deemed to have occurred when a pair of photons generated by the positron-electron annihilation are detected within a coincidence time window, e.g., within 6 to 12 nanoseconds. An LOR corresponding to the coincidence event may include a line connecting two detectors detecting and/or registering the pair of photons. The LOR may indicate a traveling path of the pair of photons.

For example, the PET dataset may include a plurality of LORs relating to the subject, a plurality of coincidence events relating to the subject, location information of a plurality of coincidence events relating to the subject, or the like, or any combination thereof. In some embodiments, time information may include a time-of-flight (TOF) dataset of the plurality of coincidence events. The TOF data of a coincidence event may include time points when a pair of photons corresponding to the coincidence event are detected by two of the plurality of detectors, respectively, a difference between the time points, or the like, or any combination thereof.

In some embodiments, location information of one of the plurality of coincidence events may include locations of two of the plurality of detectors that detect a pair of photons corresponding to the coincidence event, a location where the coincidence event occurs, or the like, or any combination thereof. In some embodiments, the location of a detector may be represented by a serial number of the detector. Merely by way of example, as described in connection with FIG. 1, the PET device may include one or more detector rings, each of which may have multiple detectors. Each of the one or more detector rings may have a first serial number, and each of the multiple detectors in a ring may have a second serial number. The location of the detector may be represented by the first serial number and the second serial number.

In some embodiments, the PET device may acquire the PET dataset by scanning at least a portion of the subject. For example, the PET device may acquire the PET dataset by scanning the entire subject. Accordingly, the PET dataset may include a PET dataset of the entire subject. As another example, the PET device may acquire the PET dataset by scanning a part of the subject. The PET dataset may include a PET dataset of the part of the subject. In some embodiments, the PET data may be analyzed when the PET device acquires the PET data in real-time. In some embodiments, the PET data to be analyzed may be acquired by the PET device in advance. The processing device 140 may obtain the PET data from the PET device or a storage device where the PET data is stored.

In some embodiments, the PET dataset may be acquired when a couch (e.g., the couch 114) supporting the subject moves within a time period. For example, the PET dataset may be acquired by scanning the subject using the PET device for the time period when the subject is moved within the detection region (e.g., the detection region 117 as illustrated in FIG. 1) of the PET device by moving the couch on which the subject is supported. In some embodiments, the movement of the couch may be continuous during at least part of the time period. For example, the couch may continuously move within the time period. As another example, the couch may move according to a step-and-shoot mode, e.g., repetitions of moving to a position and pausing for a while within the time period. In some embodiments, a direction in which the couch moves may be along the axial dimension of the PET device (e.g., the X-axis direction illustrated in FIG. 1). For example, the couch may move along the positive X-axis direction or the negative X-axis direction. As another example, the couch may move back and forth along the X-axis direction. In some embodiments, the couch may move at a constant velocity or a varying velocity, e.g., a velocity that changes with time.

In 520, the processing device 140 (e.g., the activity distribution determination module 420) may determine an activity distribution set of the tracer species in the subject within the time period. As described in connection with FIG. 1 and/or operation 510, positrons emitted by the tracer species may be annihilated with electrons in the subject, that is, annihilation events have occurred in the subject. In some embodiments, different positions of the subject may have different uptake of the tracer species, that is, different counts of the annihilation events have occurred at different positions of the subject. The activity distribution set may correspond to a distribution set of the uptake of the tracer species at different positions of the subject or a distribution set of the annihilation events having occurred at different positions of the subject. Take a living subject as an example, the uptake of the tracer species in different parts of the living subject may relate to a physiological property of each of the parts of the living subject. For example, the head or the bladder may each have a higher uptake of the tracer species than other parts of the living subject. As another example, a part of the living subject with a tumor (e.g., a benign tumor, a malignant tumor) may have a higher uptake of the tracer species compared to a reference uptake. The reference uptake may be an uptake when the part of the living subject is healthy, an uptake of a surrounding portion of the part, an uptake set by a user (e.g., a doctor) or set automatically based on prior knowledge, etc.

In some embodiments, the activity distribution set may include a plurality of segment activity distributions. Each of the plurality of segment activity distributions may correspond to one of a plurality of time segments included in the time period and one of a plurality of PET sub datasets included in the PET dataset. In some embodiments, the uptake of the tracer species at a position of the subject may be represented by a count of coincidence events having occurred at the position detected by the plurality of detectors in the PET device. Accordingly, the processing device 140 may determine the activity distribution set based on the plurality of coincidence events included in the PET dataset.

In some embodiments, the activity distribution set may include an activity distribution set of the tracer species in the subject along the direction in which the couch moves. Accordingly, the processing device 140 may determine the activity distribution set based on coincidence events having occurred along the direction. More detailed descriptions of determining the activity distribution set can be found elsewhere in the present disclosure. See, e.g., FIG. 6 and the descriptions thereof.

In 530, the processing device 140 (e.g., the offset determination module 430) may determine an offset (e.g., a position offset) of the couch (also referred to as a couch offset) within a second time segment (or a corresponding PET data subset) of the time period with respect to a first time segment (or a corresponding PET data subset) of the time period based on the activity distribution set of the tracer species. In some embodiments, the processing device 140 may also determine a distribution curve set based on the activity distribution set, and further determine the offset of the couch based on thereof. In some embodiments, values in the X-axis of the distribution curve set may represent position information of positions along the direction, and values in the Y-axis of the distribution curve set may represent uptake of the tracer species in cross-sections of the subject perpendicular to the direction. In some embodiments, each of the values in the Y-axis of the distribution curve set may include the count of coincidence events having occurred in a corresponding cross-section of the subject perpendicular to the direction. For example, the coincidence events having occurred in the corresponding cross-section may include coincidence events having occurred in different positions of the corresponding cross-section. Each of the values in the X-axis of the distribution curve set may be expressed in terms of a value in the length dimension along the direction (e.g., centimeter, millimeter) or a dimensionless value (e.g., a normalized value).

Similar to the activity distribution set, the distribution curve set may include a plurality of section distribution curves each of which may correspond to one of the plurality of segment activity distributions. The processing device 140 may determine the couch offset based on the plurality of section distribution curves. In some embodiments, at least two PET sub datasets may correspond to coincidence events having occurred at regions of the subject that at least partially overlap. For example, a first PET sub dataset may correspond to coincidence events having occurred at the head and the neck of the subject, while a second PET sub dataset may correspond to coincidence events having occurred at the neck and the chest of the subject. Accordingly, both the first PET sub dataset and the second PET sub dataset include data corresponding to coincidence events having occurred at the neck of the subject.

Assuming that efficiencies of the plurality of detectors of the PET device are uniform, a segment activity distribution of the tracer species for a same region (e.g., an overlapping region whose data are acquired at different couch positions) of the subject may be essentially the same when the same region of the subject is moved to different positions of the detection region (e.g., detection region 117 as illustrated in FIG. 1) of the PET device and scanned. As used herein, the efficiency of a detector refers to the capability or sensitivity for detecting photons by the detector. In some embodiments, the greater the capability or sensitivity for detecting photons is, the greater the efficiency of the detector may be. Thus, a part of each of the plurality of segment activity distributions relating to PET sub datasets that correspond to a same region (an overlapping region) of the subject may be the same. A segment activity distribution may be represented in the form of a section distribution curve. The section distribution curve may be a one-dimensional function along the X-axis. The only difference between different section distribution curves (or a portion of each of the section distribution curves) corresponding to a same region of the subject may be an offset between the section distribution curves along the X-axis. For brevity, two section distribution curves that correspond to a same region of a subject are referred to as two corresponding section distribution curves. For brevity, portions of two section distribution curves in which a portion from each of the section distribution curves corresponds to a same region of a subject are referred to as corresponding portions of the section distribution curves. For brevity, an offset between corresponding section distribution curves (or corresponding portions of the section distribution curves) is referred to as a distribution curve offset.

In some embodiments, the processing device 140 may determine an offset between corresponding section distribution curves (or corresponding portions of the section distribution curves) by registering the corresponding section distribution curves (or the corresponding portions of the section distribution curves) using a registration algorithm. For example, the registration algorithm may include a least squares technique, a correlation coefficient technique, or the like, or any combination thereof. In some embodiments, based on a distribution curve offset between two corresponding section distribution curves (or corresponding portions of the section distribution curves), a corresponding offset of the couch may be determined. For instance, a distribution curve offset may be equal to a corresponding offset of the couch.

As used herein, the first time segment and the second time segment may be two of the plurality of time segments. The plurality of segment activity distributions may include at least a first segment activity distribution corresponding to the first time segment and a second segment activity distribution corresponding to the second time segment. The distribution curve set may include at least a first section distribution curve corresponding to the first time segment and a second section distribution curve corresponding to the second time segment. The first section distribution curve and the second section distribution curve may include data of a same region of the subject. The processing device 140 may determine an offset of the couch based on the offset between the first segment activity curve and the second segment activity curve corresponding to the same region of the subject, and the offset of the couch accordingly. For instance, the distribution curve offset may be equal to the offset of the couch. Thus, the processing device 140 may select to process a part of the PET dataset, e.g., the first PET data subset and the second PET data subset, to determine the offset of couch, thereby increasing the efficiency of the determination of the couch offset compared to using the entire PET dataset.

In some embodiments, the first time segment may partially overlap the second time segment. For example, the first time segment may be from 0-5 seconds of a one-minute time period and the second time segment may be 3-8 seconds of the time period, that is, the first PET sub dataset and the second PET sub dataset may include a same portion of the PET dataset obtained within 3-5 seconds of the time period.

In some embodiments, if the position of the couch (or referred to as couch position for brevity) at a time point or within a time segment is known, the offset of the couch between an unknown couch position and the known position may be determined based on the offset of corresponding section distribution curves (or corresponding portions of the section distribution curves) that relate to the two couch positions. As used herein, a section distribution curve, or a portion thereof, is deemed to relate to a couch position when the PET sub dataset from which the section distribution curve, or a portion thereof, is determined at the couch position. As used herein, a couch position within or corresponding to a time segment (e.g., a first time segment, a second time segment) may be equal to an average couch position within the time segment, a couch position at the beginning of the time segment, a couch position at the end of the time segment, etc. For instance, the couch may begin to move at the beginning of the first time segment from a start position (e.g., a known start position). The second time segment may be any time segment within the time period other than the first time segment. The processing device 140 may determine an offset of the couch at any time point (e.g., at the end of the second time segment) within the time period in real-time with respect to the start position based on the process 500.

In some embodiments, the couch may be stationary in a time segment; the position of the couch at different time points within the time segment may remain the same. For example, the couch may move, in a step-and-shoot mode, to different couch positions and pause for a while at each of the couch positions within the time period. In some embodiments, a time segment (e.g., the first time segment, the second time segment, etc.) may fall within a period during which the couch pauses at a couch position. The position offset of the couch within the second time segment with respect to the first time segment may include a difference between the couch position corresponding to the first time segment and the couch position corresponding to the second time segment.

In some embodiments, the couch may be moving in a time segment; the positions of the couch at different time points within the time segment may change over time. The position offset of the couch within the second time segment with respect to the first time segment may include a difference between the couch position within the first time segment and the couch position within the second time segment. In some embodiments, the larger the velocity of the couch, the smaller the time length of the time segment may be. The distance that the couch moves within the time segment may be adjusted to be relatively small or negligible such that the position of the couch at different time points within the time segment may substantially remain the same. In this case, the offset of the couch within the second time segment with respect to the first time segment may include a difference between a couch position within the first time segment (e.g., a couch position at any time point within the first time segment, an average couch position within the first time segment, etc.) and a couch position within the second time segment (e.g., a couch position at any time point within the second time segment, an average couch position within the second time segment, etc.).

In some embodiments, the processing device 140 may also determine second position information of the couch within the second time segment based on the couch offset and first position information of the couch within the time segment. As used herein, the first position information (or the second position information) of the couch may include a first position (e.g., a first couch code) within the first time segment (or a second position (e.g., a second couch code) within the second time segment) of the couch along the direction. The first couch code (or the second couch code) may include a value corresponding to the first position (or second position) of the couch or a dimensionless value (e.g., a normalized value) corresponding to the first position (or second position) of the couch. For example, the first position information may be expressed in the form of a value in the length dimension along the direction or a dimensionless value (e.g., a normalized value). In some embodiments, the first position information of the couch may be known, and the processing device 140 may determine a value representing the second position based on the first position and the couch offset.

It should be noted that the above description is merely provided for the purposes of illustration, and not intended to limit the scope of the present disclosure. In some embodiments, before determining the activity distribution set in 520, the processing device 140 may identify a first part of the PET dataset corresponding to a region of the subject, and determine the activity distribution set accordingly. In some embodiments, the uptake of the tracer species in some part of the subject may exceed an uptake threshold. For example, the uptake of the tracer species in the head, the bladder, or the like, of the subject may exceed the uptake threshold. As described in connection with 520, different parts of the subject may have different uptakes of the tracer species. A second part of the subject (e.g., human legs, upper limbs, etc.) may have a relatively low uptake of the tracer species smaller than a second uptake threshold, and a part of the distribution curve set corresponding to the second part of the subject may be negligible with respect to a part of the distribution curve set corresponding to a first part of the subject having a high uptake, which in turn may affect the accuracy of the distribution curve set, and/or the accuracy of the couch offset determined based on the offset of corresponding section distribution curves (or corresponding portions of the section distribution curves) relating to the second part of the subject. Besides, a motion of the subject and intestinal peristalsis may affect the PET dataset and/or the distribution curve set of the tracer species. Exemplary motion may include a physiological motion (e.g., respiratory motion, cardiac motion, gastrointestinal motion, motion of the diaphragm, etc.). If the part of the subject with a high uptake of the tracer species, e.g., the bladder or the head, and the effect of the motion of the subject may be negligible, thereby improving the accuracy of the determination of the couch offset based on data relating to the high-uptake part of the subject. For example, a difference between an actual couch offset and a couch offset determined based on the process 500 may be relatively small, e.g., smaller than a difference threshold.

As described above, the offset and/or position information of the couch may be determined based on the assumption that the efficiencies of the plurality of detectors in the PET device are uniform. However, in some scenarios, the efficiencies of the plurality of detectors may be non-uniform, which may affect the accuracy of the offset and/or position information of the couch determined above. In some embodiments, the non-uniform efficiencies may relate to an intrinsic property of each of the plurality of detectors, the location of each of the plurality of detectors, whether a detector is damaged, or the like, or any combination thereof. As used herein, the intrinsic property relates to, e.g., uniformity of the material, composition, surfaces, or shapes of the detectors. In some embodiments, a detector may have different efficiencies due to differences in factors including the distance between the source of a coincidence event and the detector, the angle at which a photon from a coincidence event impinging on the detector, or the like, or a combination thereof. In some embodiments, the efficiency of a detector may change due to one or more factors including, e.g., the deformability of the surface of the detector, the damage of the detector, etc. For example, when a detector is damaged, the capability of detecting photons by the detector may decrease.

In some embodiments, before determining the activity distribution set in 520, the processing device 140 may normalize the coincidence events to compensate for the effect of the non-uniform efficiencies of the plurality of detectors. For example, the processing device 110 may normalize the counts of coincidence events detected by the plurality of detectors and assess, based on the coincidence events with the normalized counts, the efficiencies of the plurality of detectors. In some embodiments, the efficiencies of the plurality of detectors may be assessed using a uniform phantom. As used herein, a uniform phantom has a substantially constant uptake of the tracer species at all positions of the uniform phantom. As used herein, a substantially constant uptake of the tracer species by a phantom indicates that the variation between the uptakes of the tracer species throughout the phantom is below a threshold, e.g., below 20%, or below 10%, etc. In some embodiments, an efficiency distribution of the plurality of detectors may be determined based on PET data acquired by scanning the uniform phantom. The determination may be performed by the processing device 140, or by a different processing device. For example, the PET device may scan the uniform phantom which may pass the entire FOV of the PET device and a PET dataset relating to the uniform phantom may be obtained. The processing device 140 may determine the efficiency distribution based on the PET dataset relating to the uniform phantom.

In some scenarios, the offset and/or the position information of the couch may be used to filter out incorrect LORs and/or coincidence events. For example, when the couch moves to a position, a specific part of the subject may be scanned. If photons corresponding to one or more LORs and/or coincidence events detected by the plurality of detector does not belong to the specific part of the subject, the one or more LORs and/or coincidence events may be filtered out. The filtered LORs and/or coincidence events may be further processed for implementing functions including, e.g., determining parameters associated with efficiency normalization of the PET device, PET image reconstruction, etc.

In some scenarios, prior to image reconstruction, one or more parameters associated with the efficiency normalization of the detectors of the PET device may be determined and further used for image reconstruction. During image reconstruction, the one or more parameters associated with the efficiency normalization of the detectors of the PET device may be used to correct PET data acquired by the PET device due to non-uniform response of the plurality of detectors of the PET device and an image may be generated based on the corrected PET data. In some embodiments, the couch offset and/or the position information of the couch may be used to determine at least one of the one or more parameters associated with the efficiency normalization of the detectors of the PET device. For example, the at least one of the one or more parameters may include a plurality of efficiencies of the plurality of detectors of the PET device, an efficiency distribution of the plurality of detectors of the PET device, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, in 530, the processing device 140 may simultaneously determine two or more offsets of the couch for two or more pairs of time segments. In some embodiments, as described above, the activity distribution set may be represented in the form of the activity distribution curve set. The activity distribution curve set may include the plurality of section activity distribution curves each of which corresponds to one of the plurality of segment activity distributions. In 520, the processing device 140 may acquire the activity distribution curve. In 530, the processing device 140 may determine an offset (e.g., a position offset) of the couch based on the plurality of section activity distribution curves.

Figure 6:
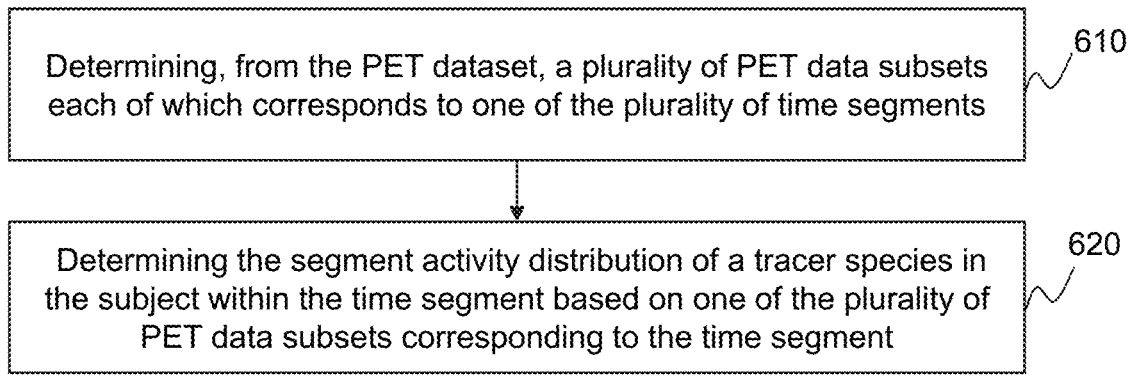
FIG. 6 is a flowchart illustrating an exemplary process for determining a segment activity distribution of a tracer species in a subject according to some embodiments of the present disclosure.

FIG. 6 is a flowchart illustrating an exemplary process for determining a segment activity distribution of a tracer species in a subject according to some embodiments of the present disclosure. In some embodiments, the process 600 may be implemented in the PET system 100 illustrated in FIG. 1. For example, the process 600 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing devices 140. The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. In some embodiments, operation 520 illustrated in FIG. 5 may be implemented based on the process 600.

In 610, the processing device 140 (e.g., the activity distribution determination module 420) may determine a plurality of PET data subsets from the PET dataset illustrated in FIG. 5. Each of the plurality of data subsets may correspond to one of the plurality of time segments included in the time period illustrated in FIG. 5. In some embodiments, the plurality of PET data subsets may constitute at least a part of the PET dataset. For example, the processing device 140 may divide the PET dataset into the plurality of PET data subsets. As another example, the plurality of PET data subsets may constitute a part of the PET dataset. In some embodiments, the part of the PET dataset may include PET dataset of a part of the subject. For example, the part of the subject may have the uptake of the tracer species exceeding an uptake threshold, e.g., the head, the bladder, etc.

In some embodiments, two subsequent time segments of the plurality of time segments may partially overlap. For example, if the time period includes a first time segment, a second time segment, a third time segment . . . , in sequence, the first time segment may partially overlap the second time segment. A first PET sub dataset corresponding to the first time segment and a second PET sub dataset corresponding to the second time segment may include portions of the PET dataset obtained within an overlapping portion of the first time segment and the second time segment. For example, the first time segment may be from 0-5 seconds of a 5-minute time period and the second time segment may be 3-8 seconds of the time period, that is, the first PET sub dataset and the second PET sub dataset may include portions of the PET dataset obtained in 3-5 seconds of the time period.

In some embodiments, a time length of each of the plurality of time segments may be the same. For example, the time period may be 30 seconds, and the time length of each of the plurality of time segments may be 100 milliseconds. In some embodiments, the time length of each of the plurality of time segments may be different. For example, the couch may move, in a step-and-shoot mode, to different couch positions and pause for a while at each of the couch positions within the time period. In some embodiments, a time segment may fall within a period during which the couch pauses at a couch position. In some embodiments, the time length of each of the plurality of time segments may be default settings in the PET system 100, or set by the PET system 100 or a user. In some embodiments, the time length may be determined and/or adjusted based on one or more factors, e.g., the velocity of the couch, the accuracy of the couch offset determined in 530, the accuracy of the second position information determined in 530, etc. For example, if the velocity of the couch is smaller than or equal to a velocity threshold, the time length may be set as 100 milliseconds. In some embodiments, the larger the velocity of the couch, the smaller the time length of the time segment may be, and a distance that the couch moves within the time segment may be relatively small or negligible such that the accuracy of the determined couch offset may satisfy an accuracy requirement. The accuracy requirement may be default settings in the PET system 100, or set by the PET system 100 or a user. In some embodiments, provided that the accuracy requirement is satisfied, the efficiency for determining the offset of the couch illustrated in FIG. 5 may be adjusted or improved by adjusting or increasing a time length of a time segment involved in the couch offset determination.

In 620, the processing device 140 (e.g., the activity distribution determination module 420) may determine a segment activity distribution of the tracer species in the subject within a time segment based on one of the plurality of PET data subsets corresponding to the time segment. As described in connection with FIG. 5, the segment activity distribution may include a segment activity distribution of the tracer species in the subject along the direction illustrated in FIG. 5 (e.g., the X-axis direction illustrated in FIG. 1). The processing device 140 may determine the segment activity distribution based on coincidence events (also referred to as "segment coincidence event") along the direction identified within the time segment. In some embodiments, the processing device 140 may identify the segment coincidence events from the plurality of coincidence events relating to the subject included in the PET dataset. For example, the segment coincidence events may be detected by detectors in the PET device along the direction within the time segment. Accordingly, the processing device 140 may designate a coincidence event among the plurality of coincidence events corresponding to a pair of photons detected by the detectors within the time segment as one of the segment coincidence events.

In some embodiments, the processing device 140 may determine the segment activity distribution based on segment coincidence events having occurred in one or more cross-sections (also referred to as "direct slice") of the subject perpendicular to the direction in which the couch moves among the segment coincidence events identified within the time segment. As used herein, a segment coincidence event having occurred in a cross-section may indicate that a pair of photons corresponding to the segment coincidence event may be detected by two detectors in the same detector ring within the time segment, that is, an LOR corresponding to the segment coincidence event may be perpendicular to the direction.

In some embodiments, the processing device 140 may determine the segment activity distribution based on location information of the segment coincidence events. For example, location information of each of the segment coincidence events may include a location where the segment coincidence event occurs at an LOR corresponding to the segment coincidence event. In some embodiments, the location may be expressed in terms of an absolute location or a dimensionless value (e.g., a normalized value).

In some embodiments, the processing device 140 may determine the location information of the segment coincidence events based on a time-of-flight (TOF) dataset of the plurality of coincidence events. For example, as described in connection with operation 510, the TOF dataset of a coincidence event may include times when a pair of photons corresponding to the coincidence event are detected by two of the plurality of detectors, respectively, a difference between the times, etc. For example, if the time difference is 0, the coincidence event may be deemed to occur in the center of an LOR corresponding to the coincidence event. Further, the processing device 140 may determine a position of the coincidence event along the X-axis illustrated in FIG. 1 based on the location information of the coincidence event.

As described in connection with 520, the activity distribution set may correspond to the distribution set of the uptake of the tracer species at different positions of the subject. The uptake of the tracer species at a position of the subject may be represented by a count of coincidence events having occurred at the position detected by the plurality of detectors in the PET device. The processing device 140 may determine the uptake of the tracer species in the one or more cross-sections based on the segment coincidence events having occurred in the one or more cross-sections and/or the location information of the segment coincidence event and further determine the segment activity distribution based on the uptake of the tracer species.

In some embodiments, the accuracy for determining the segment activity distribution using only the segment coincidence events having occurred in the one or more cross-sections may satisfy an accuracy requirement. By identifying only the segment coincidence events having occurred in the one or more cross-sections, the speed of the determination of the segment activity distribution may increase compared to using all of the segment coincidence events identified within the time segment based on the location information. On the other hand, since the segment coincidence events having occurred in the one or more cross-sections may be a part of the segment coincidence events identified within the time segment, the segment activity distribution determined based on the segment coincidence events may be more accurate than based on the segment coincidence events having occurred in the one or more cross-sections.

Figure 7:
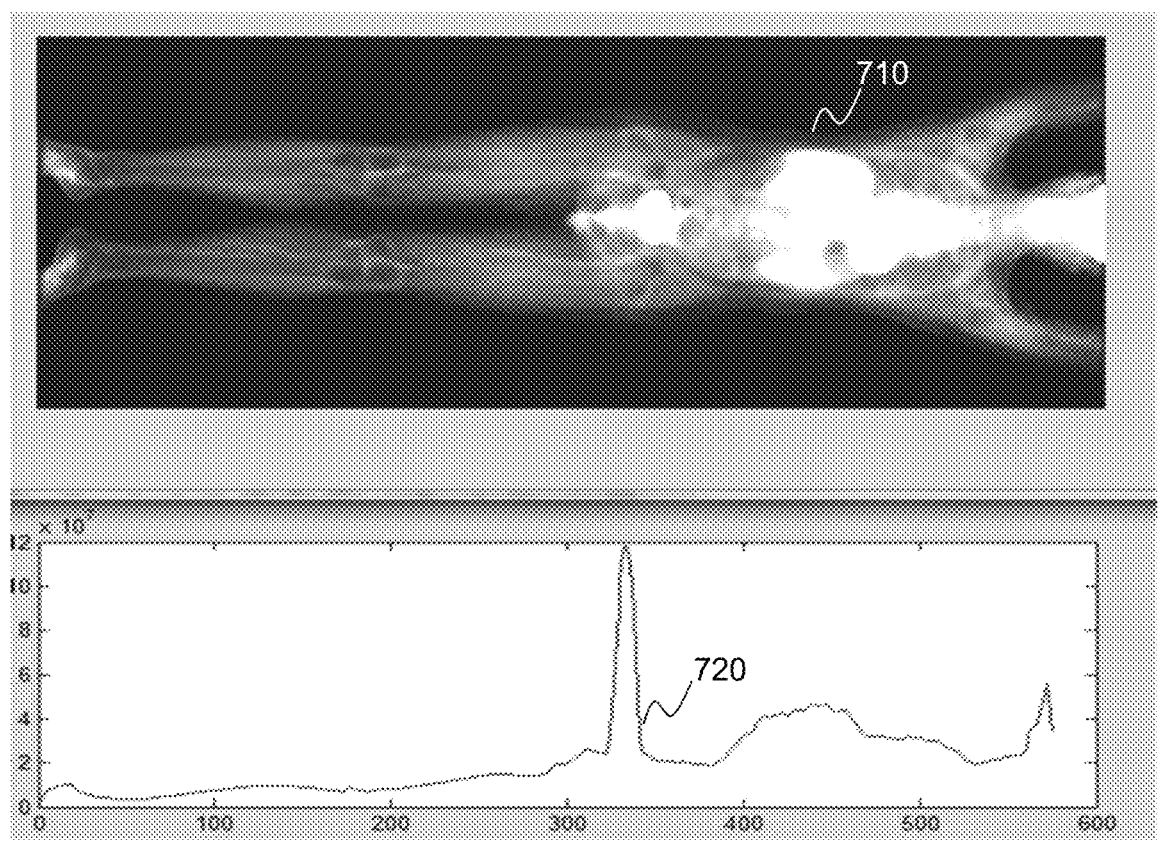
FIG. 7 is a schematic diagram illustrating an exemplary section distribution curve of a tracer species in a subject according to some embodiments.

FIG. 7 is a schematic diagram illustrating an exemplary section distribution curve of a tracer species in a subject according to some embodiments of the present disclosure.

A curve 720 may be an example of the section distribution curve illustrated in FIGS. 4-6. As illustrated in FIG. 7, the curve 720 may be a section distribution curve of a tracer species in a subject 710. Values in the X-axis of the curve 720 may represent position information along a direction that a couch moves (e.g., the axial dimension of a PET device, the X-axis direction illustrated in FIG. 1). Values in the Y-axis of the curve may represent a count of coincidence events having occurred at a plurality of cross-sections of the subject 710 perpendicular to the direction that the couch moves. The brighter a part of the subject 710 is, the greater the uptake of the tracer species in the part of the subject 710 may be, and the greater the count of the coincidence events having occurred in the part of the subject 710 may be.

In some embodiments of the present disclosure, a readable storage medium may be provided. The readable storage medium may store an executable program thereon. When the executable program is executed by a processor, the process for determining the offset of the couch illustrated in FIGS. 5-6 may be implemented.

In some embodiments of the present disclosure, a device for determining the offset of the couch may be provided. The device may include a memory and a processor. The memory may store an executable program. The processor may implement the process for determining the offset of the couch illustrated in FIGS. 5-6 when the processor executes the executable program.

Figure 8:
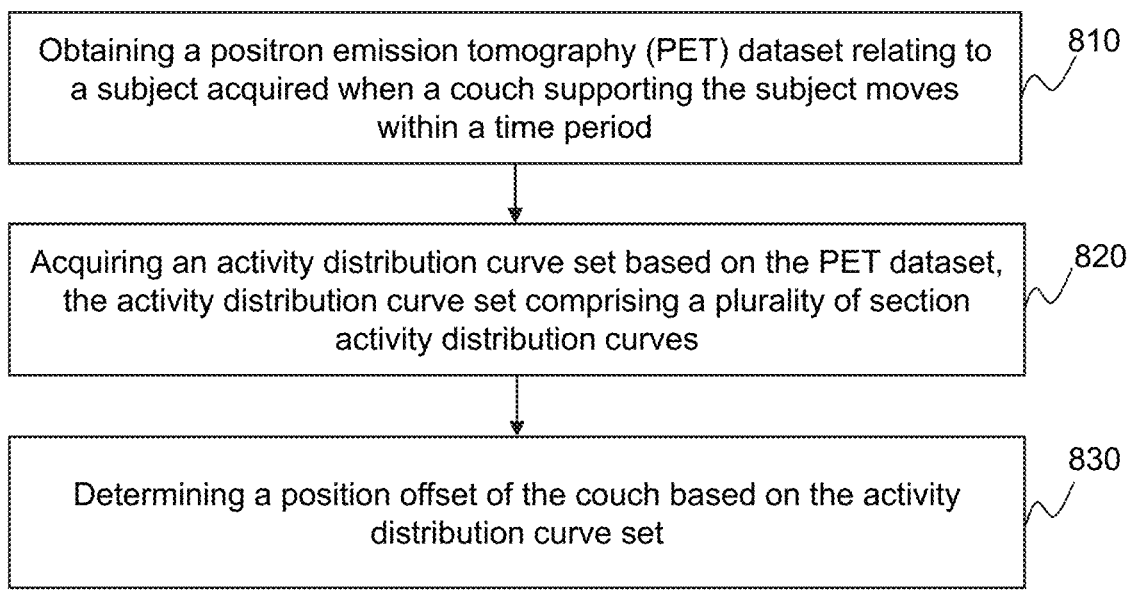
FIG. 8 is a flowchart illustrating an exemplary process for determining a position offset of a couch according to some embodiments of the present disclosure.

FIG. 8 is a flowchart illustrating an exemplary process for determining a position offset of a couch according to some embodiments of the present disclosure. In some embodiments, the process 800 may be implemented in the PET system 100 illustrated in FIG. 1. For example, the process 800 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing devices 140. The operations of the illustrated process 800 presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, the processing device 140 (e.g., the dataset obtaining module 410) may obtain a PET dataset relating to a subject acquired when a couch supporting the subject moves within a time period. Operation 810 may be similar to operation 510, the description of which is not repeated herein.

In 820, the processing device 140 (e.g., the activity distribution determination module 420) may acquire an activity distribution curve set based on the PET dataset within the time period. In some embodiments, the activity distribution curve set may include a plurality of section activity distribution curves. In the present disclosure, "activity distribution curve set" and "distribution curve set" are used interchangeably; "section activity distribution curve" and "section distribution curve" are used interchangeably. Each of the plurality of section activity distribution curves may correspond to one of a plurality of time segments included in the time period and one of a plurality of PET sub datasets included in the PET dataset. In some embodiments, two subsequent time segments of the plurality of time segments may partially overlap.

In some embodiments, a time length of each of the plurality of time segments may be the same. For example, the time period may be 30 seconds, and the time length of each of the plurality of time segments may be 100 milliseconds. In some embodiments, the time length of each of the plurality of time segments may be different. For example, the couch may move, in a step-and-shoot mode, to different couch positions and pause for a while at each of the couch positions within the time period. In some embodiments, a time segment may fall within a period during which the couch pauses at a couch position. More detailed descriptions of acquiring the activity distribution curve set can be found elsewhere in the present disclosure, e.g., FIGS. 5-6 and the descriptions thereof.

In 830, the processing device 140 (e.g., the offset determination module 430) may determine a position offset of the couch based on the activity distribution curve set. As described in operation 820, the activity distribution curve set may include a plurality of section activity distribution curves. The processing device 140 may determine the position offset based on the plurality of section activity distribution curves. Assuming that efficiencies of the plurality of detectors of the PET device are (substantially) uniform, a part of each of the plurality of section activity distribution curves relating to PET sub datasets that correspond to a same region (an overlapping region) of the subject may be (substantially) the same. The activity section distribution curve may be a one-dimensional function along a direction in which the couch moves (e.g., the axial dimension of the PET device, the X-axis direction illustrated in FIG. 1). The only difference between different section activity distribution curves (or a portion of each of the section distribution curves) corresponding to a same region of the subject may be an offset (also referred to "distribution curve offset") between the section activity distribution curves along the X-axis. In some embodiments, the activity distribution curve offset may be equal to a position offset of the couch corresponding to the section activity distribution curves. For example, the plurality of section activity distribution curves may include a first section activity distribution curve corresponding to a first time segment (or a corresponding PET data subset) and a second activity distribution curve corresponding to a second time segment (or a corresponding PET data subset). The first section activity distribution curve and the second section activity distribution curve may include data of a same region of the subject. An offset between the first section activity distribution curve and the second activity distribution curve may be equal to a position offset of the couch within the second time segment with respect to the first time segment. More detailed descriptions of determining the position offset of the couch based on the activity distribution curve set can be found elsewhere in the present disclosure, e.g., FIGS. 5-6, and the descriptions thereof.

In some embodiments, the processing device 140 may also determine a couch code of the couch based on the position offset and a reference couch code. As used herein, a couch code may include a value corresponding to a position of a couch or a dimensionless value (e.g., a normalized value) corresponding to the position of the couch. In some embodiments, the first time segment and the second time segment may be any two of the plurality of time segments. A first couch code corresponding to the first time segment may be a known, reference couch code. The processing device 140 may determine a second couch code corresponding to the second time segment based on the first couch code and the position offset within the second time segment with respect to the first time segment. For example, the couch may begin to move at the beginning of the first time segment from a start position (e.g., a known start position). The second time segment may be any time segment within the time period other than the first time segment. The processing device 140 may determine a position offset of the couch at any time point (e.g., at the end of the second time segment) within the time period in real-time with respect to the start position based on the process 800.

As described above, the position offset and/or position information of the couch may be determined based on the assumption that the efficiencies of the plurality of detectors in the PET device are uniform. However, in some scenarios, the efficiencies of the plurality of detectors may be non-uniform, which may affect the accuracy of the position offset and/or position information of the couch determined above. In some embodiments, before the activity distribution curve set is determined (e.g., as in 820), the processing device 140 may normalize coincidence events to compensate for the effect of the non-uniform efficiencies of the plurality of detectors and determine the activity distribution curve set accordingly. More detailed descriptions of normalizing the coincidence events can be found elsewhere in the present disclosure, e.g., FIGS. 4 and 5, and the descriptions thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device including a set of instructions;

at least one processor in communication with the at least one storage device, wherein when executing the set of instructions, the at least one processor is configured to cause the system to perform operations including:

obtaining a positron emission tomography (PET) dataset relating to a subject acquired, based on a tracer species in the subject, by a positron emission tomography (PET) device, wherein the PET dataset includes data relating to a plurality of coincidence events generated by the subject, a count of one or more coincidence events, among the plurality of coincidence events, having occurred at a position of the subject represents uptake of the tracer species at the position of the subject, and the PET dataset relating to the subject is acquired for a time period when the subject moves by moving, along a direction parallel with an axial dimension of the PET device, a couch on which the subject is supported, the time period comprising a plurality of time segments including a first time segment and a second time segment;

determining, based on at least a portion of the plurality of coincidence events relating to the subject, an activity distribution set of the tracer species in the subject within the time period, the activity distribution set including a plurality of segment activity distributions, each of the plurality of segment activity distributions corresponding to one of the plurality of time segments included in the time period and one of a plurality of PET data subsets included in the PET dataset, the each of the plurality of segment activity distributions being represented by one of a plurality of section activity distribution curves, values in an X-axis of each of the plurality of section activity distribution curves representing position information of positions along the direction in which the couch moves, values in a Y-axis of the each of the plurality of section activity distribution curves representing uptake of the tracer species in one or more cross-sections of the subject perpendicular to the direction, and the section activity distribution curve being one dimensional function with respect to the values in the X-axis; and determining an offset of the couch along the axial dimension of the PET device within the second time segment with respect to the first time segment based on the activity distribution set of the tracer species, including:

determining, from the plurality of segment activity distributions, a first segment activity distribution and a second segment activity distribution, the first segment activity distribution corresponding to the first time segment and a first PET data subset of the plurality of PET data subset, the second segment activity distribution corresponding to the second time segment and a second PET data subset of the plurality of PET data subsets, a portion of the first PET data subset and a portion of the second PET data subset corresponding to coincidence events having occurred at a same region of the subject but different time segments, the first segment activity distribution being represented by a first section activity distribution curve, and the second segment activity distribution being represented by a second section activity distribution curve;

determining a position difference along the X-axis between a portion of the first section activity distribution curve corresponding to the coincidence events having occurred at the same region of the subject and a portion of the second section activity distribution curve corresponding to the coincidence events having occurred at the same region of the subject by registering the first section activity distribution curve and the second section activity distribution curve, uptake of the tracer species at the same region of the subject being substantially the same, and the position difference along the X-axis between the portion of the first section activity distribution curve and the portion of the second section activity distribution curve being an offset along the direction between the portions of the first section activity distribution curve and the second section activity distribution curve; and designating the position difference along the X-axis as the offset of the couch along the direction within the second time segment with respect to the first time segment; and performing PET image reconstruction by filtering out, based on the offset of the couch, one or more incorrected events among the plurality of coincidence events.

2. The system of claim 1, wherein the determining an activity distribution set of the tracer species in the subject within the time period includes:

for each of at, least two of the plurality of time segments, determining a segment activity distribution of the plurality of segment activity distributions of the tracer species in the subject within the time segment, the at least two of the plurality of time segments comprising the first time segment and the second time segment.

3. The system of claim 2, wherein the determining an activity distribution set of the tracer species in the subject within the time period further includes:

for each of the at least two of the plurality of time segments, the determining a segment activity distribution of the plurality of segment activity distributions of the tracer species in the subject within the time segment includes determining the segment activity distribution of the tracer species in the subject within the time segment based on one of the plurality of PET data subsets corresponding to the time segment.

4. The system of claim 1, wherein the at least one processor is further configured to cause the system to perform the operations including:

obtaining first position information of the couch within the first time segment; and determining second position information of the couch within the second time segment based on the first position information and the offset of the couch.

5. The system of claim 4, wherein the determining an activity distribution set of the tracer species in the subject within the time period includes:

determining the plurality of time segments based on at least one of a velocity of the couch or an accuracy of the second position information.

6. The system of claim 1, wherein the determining an activity distribution set of the tracer species in the subject within the time period includes:

identifying, based on the PET dataset, coincidence events along the direction in which the couch moves; and determining the activity distribution set of the tracer species in the subject based on the coincidence events along the direction in which the couch moves.

7. The system of claim 6, wherein the determining an activity distribution set of the tracer species in the subject based on the coincidence events along the direction in which the couch moves includes:
identifying, among the coincidence events along the direction in which the couch moves, coincidence events occurred in the one or more cross-sections of the subject perpendicular to the direction in which the couch moves; and
determining the activity distribution set of the tracer species in the subject based on the identified coincidence events occurred in the one or more cross-sections of the subject perpendicular to the direction in which the couch moves.

8. The system of claim 6, wherein the determining an activity distribution set of the tracer species in the subject based on the coincidence events along the direction in which the couch moves includes:
determining a time-of-flight (TOF) dataset of the coincidence events along the direction in which the couch moves;
determining location information of the coincidence events along the direction in which the couch moves based on the time-of-flight (TOF) dataset; and
determining the activity distribution set of the tracer species in the subject based on the location information of the coincidence events along the direction in which the couch moves.

9. The system of claim 6, wherein the at least one processor is configured to cause the system to perform additional operations including:
normalizing the coincidence events along the direction in which the couch moves; and
determining the activity distribution set of the tracer species in the subject based on the normalized coincidence events along the direction in which the couch moves.

10. The system of claim 9, the PET device comprising a plurality of detectors, wherein the normalizing the coincidence events along the direction in which the couch moves includes:
determining an efficiency distribution of the plurality of detectors based on a uniform phantom; and
normalizing the coincidence events along the direction in which the couch moves based on the efficiency distribution.

11. The system of claim 1, wherein the determining an activity distribution set of the tracer species in the subject within the time period includes:
identifying a part of the PET dataset corresponding to a region of the subject; and
determining the activity distribution set of the tracer species in the subject based on the identified part of the PET dataset.

12. The system of claim 11, wherein the region of the subject includes at least one of the head or the bladder of the subject.

13. A method implemented on a computing device having at least one processor, and at least one storage device, the method comprising:
obtaining a positron emission tomography (PET) dataset relating to a subject acquired, based on a tracer species in the subject, by a positron emission tomography (PET) device, wherein the PET dataset includes data relating to a plurality of coincidence events generated by the subject, a count of one or more coincidence events, among the plurality of coincidence events, having occurred at a position of the subject represents uptake of the tracer species at the position of the subject, and the PET dataset relating to the subject is acquired for a time period when the subject moves by moving, along a direction parallel with an axial dimension of the PET device, a couch on which the subject is supported, the time period comprising a plurality of time segments including a first time segment and a second time segment;
determining, based on at least a portion of the plurality of coincidence events relating to the subject, an activity distribution set of the tracer species in the subject within the time period, the activity distribution set including a plurality of segment activity distributions, each of the plurality of segment activity distributions corresponding to one of the plurality of time segments included in the time period and one of a plurality of PET data subsets included in the PET dataset, the each of the plurality of segment activity distributions being represented by one of a plurality of section activity distribution curves, values in an X-axis of each of the plurality of section activity distribution curves representing position information of positions along the direction in which the couch moves, values in a Y-axis of the each of the plurality of section activity distribution curves representing uptake of the tracer species in one or more cross-sections of the subject perpendicular to the direction, and the section activity distribution curve being one dimensional function with respect to the values in the X-axis;
determining an offset of the couch along the axial dimension of the PET device within the second time segment with respect to the first time segment based on the activity distribution set of the tracer species, including:
determining, from the plurality of segment activity distributions, a first segment activity distribution and a second segment activity distribution, the first segment activity distribution corresponding to the first time segment and a first PET data subset of the plurality of PET data subset, the second segment activity distribution corresponding to the second time segment and a second PET data subset of the plurality of PET data subsets, a portion of the first PET data subset and a portion of the second PET data subset corresponding to coincidence events having occurred at a same region of the subject but different time segments, the first segment activity distribution being represented by a first section activity distribution curve, and the second segment activity distribution being represented by a second section activity distribution curve;
determining a position difference along the X-axis between a portion of the first section activity distribution curve corresponding to the coincidence events having occurred at the same region of the subject and a portion of the second section activity distribution curve corresponding to the coincidence events having occurred at the same region of the subject by registering the first section activity distribution curve and the second section activity distribution curve, uptake of the tracer species at the same region of the subject being substantially the same, and the position difference along the X-axis between the portion of the first section activity distribution curve and the portion of the second section activity distribution curve being an offset along the direction between the portions of the first section activity distribution curve and the second section activity distribution curve; and designating the position difference along the X-axis as the offset of the couch along the direction within the second time segment with respect to the first time segment; and performing PET image reconstruction by filtering out, based on the offset of the couch, one or more incorrected events among the plurality of coincidence events.

14. A system, comprising:

at least one storage device including a set of instructions;

at least one processor in communication with the at least one storage device, wherein when executing the set of instructions, the at least one processor is configured to cause the system to perform operations including:

obtaining a positron emission tomography (PET) dataset relating to a subject acquired, based on a tracer species in the subject, by a positron emission tomography (PET) device, wherein the PET dataset includes data relating to a plurality of coincidence events generated by the subject, a count of one or more coincidence events, among the plurality of coincidence events, having occurred at a position of the subject represents uptake of the tracer species at the position of the subject, and the PET dataset relating to the subject is acquired for a time period when the subject moves by moving, along a direction parallel with an axial dimension of the PET device, a couch on which the subject is supported, the time period comprising a plurality of time segments including a first time segment and a second time segment;

determining an activity distribution curve set of the tracer species in the subject within the time period based on at least a portion of the plurality of coincidence events relating to the subject, the activity distribution curve set comprising a plurality of section activity distribution curves, each of the plurality of section activity distribution curves corresponding to one of the plurality of time segments included in the time period and one of a plurality of PET data subsets included in the PET dataset, values in an X-axis of the each of the plurality of section activity distribution curves representing position information of positions along the direction in which the couch moves, values in a Y-axis of the each of the plurality of section activity distribution curves representing uptake of the tracer species in one or more cross-sections of the subject perpendicular to the direction, and the section activity distribution curve being one dimensional function with respect to the values in the X-axis; and determining an offset of the couch along the axial dimension of the PET device within the second time segment with respect to the first time segment based on the activity distribution curve set of the tracer species, including:

determining, from the plurality of section activity distribution curves, a first section distribution curve and a second section distribution curve, the first section distribution curve corresponding to the first time segment and a first PET data subset of the plurality of PET data subset, the second section distribution curve corresponding to the second time segment and a second PET data subset of the plurality of PET data subsets, a portion of the first PET data subset and a portion of the second PET data subset corresponding to coincidence events having occurred at a same region of the subject but different time segments, and uptake of the tracer species at the same region of the subject being substantially the same;

determining, by registering the first section activity distribution curve and the second section activity distribution curve, a distribution curve offset between a portion of the first section distribution curve corresponding to the coincidence events having occurred at the same region of the subject and a portion of the second section distribution curve corresponding to the coincidence events having occurred at the same region of the subject along the direction; and designating the distribution curve offset as the offset of the couch along the direction within the second time segment with respect to the first time segment; and performing PET image reconstruction by filtering out, based on the offset of the couch, one or more incorrected events among the plurality of coincidence events.

15. The system of claim 14, wherein the system is further directed to perform the operations including:

determining a couch code of the couch based on the offset of the couch and a reference couch code.

16. The system of claim 14, wherein the at least one processor is further configured to cause the system to perform the operations including:

obtaining first position information of the couch within the first time segment; and determining second position information of the couch within the second time segment based on the first position information and the offset of the couch.

17. The system of claim 14, wherein the determining an activity distribution curve set of the tracer species in the subject within the time period includes includes:

determining the plurality of time segments based on at least one of a velocity of the couch or an accuracy of the second position information.

18. The system of claim 14, wherein the determining an activity distribution curve set of the tracer species in the subject within the time period includes includes:

identifying, based on the PET dataset, coincidence events along the direction in which the couch moves; and determining the activity distribution curve set of the tracer species in the subject based on the coincidence events along the direction in which the couch moves.

19. The system of claim 14, wherein the determining an activity distribution curve set of the tracer species in the subject within the time period includes:

identifying a part of the PET dataset corresponding to a region of the subject; and determining the activity distribution curve set of the tracer species in the subject based on the identified part of the PET dataset.

20. The system of claim 19, wherein the region of the subject includes at least one of the head or the bladder of the subject.

* * * * *